United States Patent [19]

Bäther

[11] Patent Number: 4,844,867
[45] Date of Patent: Jul. 4, 1989

[54] COLORIMETRIC DETECTOR

[75] Inventor: Wolfgang Bäther, Lübeck, Fed. Rep. of Germany

[73] Assignee: Drägerwerk Aktiengesellschaft, Lübeck, Fed. Rep. of Germany

[21] Appl. No.: 52,787

[22] Filed: May 20, 1987

[30] Foreign Application Priority Data

May 21, 1986 [DE] Fed. Rep. of Germany ....... 3617023

[51] Int. Cl.$^4$ .......................... G01N 1/48; G01N 21/06
[52] U.S. Cl. ........................................ 422/60; 422/56; 422/57; 436/902
[58] Field of Search ...................... 422/55, 56, 57, 58, 422/59, 60, 86, 87; 436/902, 50, 128, 130; 252/408.1; 568/488

[56] References Cited

U.S. PATENT DOCUMENTS 4,308,028 12/1981 Elkins ..................................... 422/58
4,348,358 9/1982 McKee et al. ......................... 422/58
4,521,376 6/1985 Witonsky et al. ................. 252/408.1
4,666,859 5/1987 Attar .................................... 436/902
4,687,529 8/1987 Wang ................................... 422/58

FOREIGN PATENT DOCUMENTS 2084725 4/1982 United Kingdom .

Primary Examiner—Barry S. Richman
Assistant Examiner—T. J. Wallen
Attorney, Agent, or Firm—Walter Ottesen

[57] ABSTRACT

A colorimetric detector such as a gas dosimeter, contains a strip-like carrier with a detection reagent in a transparent housing that can be opened at least at one end thereof. The detector is expanded in terms of its use to such reagent systems in which the pigment formed diffuses beyond the reaction zone. For this purpose, the detection reagent is provided such that it is contained in impregnated tabs arranged in a row on the carrier.

12 Claims, 1 Drawing Sheet

U.S. Patent	Jul. 4, 1989	4,844,867
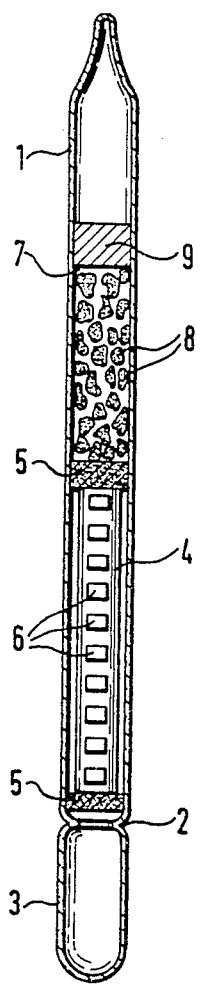

COLORIMETRIC DETECTOR

FIELD OF THE INVENTION

The invention relates to a colorimetric detector such as a gas dosimeter which contains a strip-like carrier with a detection reagent in a transparent housing. The housing can be opened on at least one end thereof.

BACKGROUND OF THE INVENTION

A gas dosimeter of this kind is disclosed in United Kingdom Pat. No. 2 084 725 B.

A strip impregnated with a detection reagent, when exposed to the gas that is to be detected, develops a color change which with sustained exposure time progresses along the strip. The colored length then represents the measure for the gas concentration that is to be detected.

Especially when measuring low concentrations of a toxic substance over a relatively long measuring period, such reagents, which provide a sensitive and specific color reaction with the gas to be detected but in which the pigment formed is soluble within the impregnation at a high diffusion rate, cannot be used as a length indicator, because instead of remaining as an indicator agent in the reaction zone, the pigment distributes out of the reaction zone into the zones where a reaction has not yet occurred, making a length reading impossible. If required, an evaluation would be possible with respect to the color saturation, but without auxiliary aids this is even more difficult and less accurate than a length reading.

SUMMARY OF THE INVENTION

It is an object of the invention to extend the use of the known gas dosimeter to such reagent systems in which the pigment formed diffuses beyond the reaction zone.

The object is attained by providing that the detection reagent is contained in impregnated tabs disposed in a row on the carrier.

The advantages attained with the invention are substantially that the tabs can be simply attached to the carrier, for example, by applying the suitably dissolved detection reagent with a pipette on fields that are equipped so as to be hydrophilic. Since the individual tabs are separated from one another by non-hydrophilic intervening spaces, a change in color of the detection reagent is restricted to one tab, and the change in color cannot spread to the next tab by mere diffusion of the reaction products within the detection reagent. Instead, it is assured that the change in color of the individual tabs can be essentially ascribed only to the action of the toxic substance.

The dimensioning and shape of the individual tabs can easily be adapted to the accuracy of the reading required. For insensitive dosimeters, for example, relatively large square tabs may be provided, whereas in contrast thereto and to increase the sensitivity, a closely spaced succession of minimum-sized tabs disposed transversely to the direction of diffusion and spaced apart by the least possible distance from one another can be provided.

By means of a succession of tabs having a different surface area, that is, a different length and/or width, instruments having inherently different sensitivity and thus a very wide measurement range can be provided; in the evaluation, tabs of different size are weighted differently.

Since the number of tabs that have changed color is now the measure of the toxic substance concentration, it is not necessary to provide a measuring scale on the housing. As a result, the costly alignment of the measuring scale with the position of the reagent layer can be dispensed with.

With the detector according to the invention, reagents which in the known equipment can be used only for a comparative measurement of depth of color can thus be used for a length measurement of the color change zone.

Advantageously, such reagents, which are present in a dissolved form, can be contained in the tabs. The tabs are easily applied onto the hydrophilic fields; because they are distributed among tabs they are retained over the entire area of the carrier in terms of their surface distribution, and in terms of a color reaction they prove to be particularly reactive.

For the case where the individual tabs have a very small amount of detection reagent applied, it is advantageous to provide a buffer chamber in the dosimeter housing, which emits volatile ingredients that could diffuse out of the tabs into the reagent space. In this way, a constant composition of the individual reagent ingredients in the tabs is assured and the detection reagents will not dry out during relatively long periods of storage.

During the use of the gas dosimeter as well, that is when the housing is opened, the volatile components of the reagent system are replenished, so that the state of equilibrium required for the detection reaction remains as at the outset.

For reagent systems that cause undesirable reactions under the influence of air during storage, it is advantageous to fill the dosimeter housing with an inert gas. This may for example be nitrogen or an oxygen-free gas mixture.

The carrier is advantageously a polyester foil which is easily impregnated with individual tabs.

Cellulose has proved to be a suitable base for the tabs. Other tab materials can, for example, be silica gel or aluminum oxide. The gas dosimeter is highly suitable for detecting formaldehyde, with the tabs being impregnated with a pararosaniline-hydrogen chloride-sulfite reagent. The course of the detection reaction in the tabs is that pararosaniline acid, catalyzed with formaldehyde, reacts to form an imine, to which sulfite ions become added, which form a sulfonic acid derivative and finally form a blue pigment.

To prevent drying out of the detection reagent, it is suitable to admix a hydrocolloid as a moisture stabilizer. This may for example comprise gelatine or pectin.

Since the sulfite formed during the pararosaniline reaction is converted by air oxidation into sulfuric acid, and sulfuric acid causes decomposition of the pigment, ascorbic acid is suitably added to the detection reagent as a sulfite oxidation inhibitor.

To prevent an air filling of the dosimeter housing causing chemical reactions in the detection reagent during the storage period, which would thwart a visible color reaction when the dosimeter is used, the dosimeter housing is advantageously filled with an oxygen-free inert gas. This is indicated particularly in the detection of formaldehyde, because during this long period, the sulfur dioxide in the reagent could oxidize, and the resultant sulfuric acid could destroy the detection reagent.

In order to assure a constant consistency of the detection reagent during the storage period as well as during the period of use of the gas dosimeter, the buffer chamber is provided with a granulated filling of silicon dioxide, which is impregnated with a solution of hydrogen chloride, sodium sulfite and water. A buffer chamber of this kind should be provided particularly if the indication sensitivity is brought about by reduction of the reagent volume in the tabs. In such a case, even slight quantities of toxic substance can be enough for a complete color reaction. The small volume of reagent is then opposed by the largest possible diffusing gas volume. In that case, the small reagent volume is no longer able to compensate for the losses of volatile components.

BRIEF DESCRIPTION OF THE DRAWING

The single figure of the drawing shows a schematic of the colorimetric gas dosimeter according to an embodiment of the invention.

DESCRIPTION OF THE PREFERRED EMBODIMENT OF THE INVENTION

The schematic shows the colorimetric gas dosimeter in a transparent tubular glass housing 1. One of its ends can be opened with a cap 3 that can be broken off at the constriction 2. A strip-like carrier 4 is received between two permeable holder elements 5, facing the openable end, in the housing 1. A plurality of square tabs 6 are mounted in succession on the carrier 4. They contain the reagent necessary for the gas measurement.

A buffer chamber 7 is provided and contains a filling 8 that is fixed in its position by means of a plug 9. The buffer chamber 7 is disposed behind the carrier 4.

It is understood that the foregoing description is that of the preferred embodiments of the invention and that various changes and modifications may be made thereto without departing from the spirit and scope of the invention as defined in the appended claims.

What is claimed is:

1. A colorimetric gas dosimeter for measuring a quantity of a gaseous substance, the colorimetric gas dosimeter comprising:
   a transparent elongated closed housing having a predetermined length;
   said housing having an end portion and a housing wall;
   means formed in said wall for facilitating a separation of said end portion from said housing so as to provide an opening in said housing for receiving a gaseous substance to be measured into said housing;
   a strip-like carrier defining a longitudinal axis and mounted in said housing so as to extend along said length thereof;
   a plurality of tabs arranged in a row on said carrier and each of said tabs containing a detecting reagent for reacting with said substance to yield reaction products which produce a change in color;
   each of said tabs and the reagent contained therein corresponding to a specific level of concentration of said substance whereby the number of tabs that have changed color is a measure of the quantity of said substance which is present; and,
   each two mutually adjacent ones of said tabs being separated from each other by a non-hydrophilic unobstructed space to prevent said reaction products from diffusing from one of said tabs to the next adjacent one of said tabs.

2. The colorimetric detecting arrangement of claim 1, said detecting reagent being in a dissolved form.

3. The colorimetric detecting arrangement of claim 1, said closed housing being filled with an inert gas.

4. The colorimetric detecting arrangement of claim 1, said strip-like carrier being made of a polyester foil.

5. The colorimetric detecting arrangement of claim 1, said strip-like carrier having a coating of cellulose material formed thereon in the region of said tabs.

6. The colorimetric detecting arrangement of claim 1, said tabs being impregnated with said detecting reagent and the latter being a pararosaniline-hydrogen chloride-sulfite reagent for detecting formaldehyde.

7. The colorimetric detecting arrangement of claim 6, wherein a hydrocolloid is admixed to said detecting reagent as a humidity stabilizer.

8. The colorimetric detecting arrangement of claim 6, wherein ascorbic acid is added to said detecting reagent as a sulfite-oxidation inhibitor.

9. The colorimetric detecting arrangement of claim 6, wherein the housing is filled with an inert gas in the form of an oxygen-free atmosphere.

10. A colorimetric gas dosimeter for measuring a quantity of a gaseous substance, the colorimetric gas dosimeter comprising:
    a transparent elongated closed housing having a predetermined length;
    said housing having an end portion and a housing wall;
    means formed in said wall for facilitating the separation of said end portion so as to provide an opening in said housing for receiving a gaseous substance to be measured into said housing;
    a strip-like carrier defining a longitudinal axis and mounted in said housing so as to extend along said length thereof;
    a plurality of tabs arranged in a row on said carrier and each of said tabs containing a detecting reagent for reacting with said substance to produce a change in color and reaction products; and,
    said detecting reagent includes volatile constituents and said arrangement further comprises a gas permeable partition interface for partitioning of said housing into first and second elongated chambers disposed one behind the other along the length of said housing; said strip-like carrier being mounted in said first chamber and said second chamber being a buffer chamber containing volatile substance means for releasing the same into said interior of said housing for assuring a constant composition of the reagent, said volatile substance means being in equilibrium with said volatile constituents of said reagent.

11. The colorimetric detecting arrangement of claim 10, wherein said buffer chamber contains a granular charge of silicon dioxide impregnated with a hydrogen chloride-sodium sulfite-water solution.

12. The colorimetric detecting arrangement of claim 3, wherein each two mutually adjacent ones of said tabs are spaced apart a predetermined distance to prevent said reaction products from diffusing from one of said tabs to the next adjacent one of said tabs.

* * * * *

UNITED STATES PATENT AND TRADEMARK OFFICE
CERTIFICATE OF CORRECTION

PATENT NO. : 4,844,867

DATED : July 4, 1989

INVENTOR(S) : Wolfgang Bäther

It is certified that error appears in the above-identified patent and that said Letters Patent is hereby corrected as shown below:

In column 4, line 64: delete "3, wherein" and substitute -- 10, wherein -- therefor.

Signed and Sealed this

Tenth Day of April, 1990

Attest:

HARRY F. MANBECK, JR.

*Attesting Officer*  *Commissioner of Patents and Trademarks*